(12) United States Patent
Minahan

(10) Patent No.: US 11,547,815 B2
(45) Date of Patent: Jan. 10, 2023

(54) SYSTEMS AND METHODS FOR MEASURING AND CONTROLLING PRESSURE WITHIN AN INTERNAL BODY CAVITY

(71) Applicant: COVIDIEN LP, Mansfield, MA (US)

(72) Inventor: Jason S. Minahan, Wilmington, MA (US)

(73) Assignee: COVIDIEN LP, Mansfield, MA (US)

( * ) Notice: Subject to any disclaimer, the term of this patent is extended or adjusted under 35 U.S.C. 154(b) by 439 days.

(21) Appl. No.: 15/992,994

(22) Filed: May 30, 2018

(65) Prior Publication Data

US 2019/0366017 A1 Dec. 5, 2019

(51) Int. Cl.
| | |
|---|---|
| *A61B 1/00* | (2006.01) |
| *A61M 13/00* | (2006.01) |
| *A61B 1/015* | (2006.01) |
| *A61B 1/303* | (2006.01) |
| *A61B 5/03* | (2006.01) |
| *A61B 1/018* | (2006.01) |
| *A61B 17/32* | (2006.01) |
| *A61B 17/42* | (2006.01) |
| *A61B 17/00* | (2006.01) |

(52) U.S. Cl.
CPC ........... *A61M 13/003* (2013.01); *A61B 1/015* (2013.01); *A61B 1/018* (2013.01); *A61B 1/303* (2013.01); *A61B 5/035* (2013.01); *A61B 17/320016* (2013.01); *A61B 2017/0034* (2013.01); *A61B 2017/00269* (2013.01); *A61B 2017/4216* (2013.01); *A61B 2217/005* (2013.01); *A61M 2205/3344* (2013.01); *A61M 2205/52* (2013.01); *A61M 2210/1433* (2013.01)

(58) Field of Classification Search
None
See application file for complete search history.

(56) References Cited

U.S. PATENT DOCUMENTS

| | | |
|---|---|---|
| 1,585,934 A | 5/1926 | Muir |
| 1,666,332 A | 4/1928 | Hirsch |
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |

(Continued)

*Primary Examiner* — Timothy J Neal
(74) *Attorney, Agent, or Firm* — Carter, DeLuca & Farrell LLP

(57) ABSTRACT

A system includes an endoscope configured for insertion into an internal body cavity and a fluid management system. The fluid management system includes a pump configured to pump fluid through the endoscope into the internal body cavity and a controller configured to determine a pressure within the internal body cavity based upon a current feedback signal received from the pump. A method includes supplying a drive signal to a pump to pump fluid into an internal body cavity, receiving a current feedback signal from the pump, and determining a pressure within the internal body cavity based on the current feedback signal.

12 Claims, 5 Drawing Sheets

(56) References Cited

U.S. PATENT DOCUMENTS

| | | |
|---|---|---|
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,650,462 A * | 3/1987 | DeSatnick ............... A61B 1/12 601/2 |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,464,391 A * | 11/1995 | DeVale ............... A61M 3/0258 604/67 |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |

(56) References Cited

U.S. PATENT DOCUMENTS

| | | |
|---|---|---|
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,663,264 B2 | 3/2014 | Cesarini et al. |
| 8,678,999 B2 | 3/2014 | Isaacson |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,125,550 B2 | 9/2015 | Shener-Irmakoglu et al. |
| 9,155,454 B2 | 10/2015 | Sahney et al. |
| 2001/0039963 A1 | 11/2001 | Spear |
| 2001/0047183 A1 | 11/2001 | Privitera |
| 2002/0058859 A1 | 5/2002 | Brommersma |
| 2002/0165427 A1 | 11/2002 | Yachia |
| 2003/0050603 A1 | 3/2003 | Todd |
| 2003/0050638 A1 | 3/2003 | Yachia |
| 2003/0078609 A1 | 4/2003 | Finlay |
| 2003/0114875 A1 | 6/2003 | Sjostrom |
| 2004/0204671 A1 | 10/2004 | Stubbs |
| 2005/0043690 A1 | 2/2005 | Todd |
| 2005/0085692 A1 | 4/2005 | Kiehn |
| 2006/0036132 A1 | 2/2006 | Renner |
| 2006/0047185 A1 | 3/2006 | Shener |
| 2006/0241586 A1 | 10/2006 | Wilk |
| 2007/0260111 A1* | 11/2007 | Baur .................. F04B 43/1253 600/101 |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams |
| 2008/0097469 A1 | 4/2008 | Gruber et al. |
| 2008/0097470 A1 | 4/2008 | Gruber et al. |
| 2008/0097471 A1 | 4/2008 | Adams |
| 2008/0135053 A1 | 6/2008 | Gruber |
| 2008/0146872 A1 | 6/2008 | Gruber |
| 2008/0146873 A1 | 6/2008 | Adams |
| 2008/0245371 A1 | 10/2008 | Gruber |
| 2008/0249366 A1 | 10/2008 | Gruber |
| 2008/0249534 A1 | 10/2008 | Gruber |
| 2008/0249553 A1 | 10/2008 | Gruber |
| 2008/0262308 A1 | 10/2008 | Prestezog |
| 2009/0082628 A1 | 3/2009 | Kucklick |
| 2009/0270812 A1 | 10/2009 | Litscher |
| 2009/0270895 A1 | 10/2009 | Churchill |
| 2009/0270896 A1 | 10/2009 | Sullivan |
| 2009/0270897 A1 | 10/2009 | Adams |
| 2009/0270898 A1 | 10/2009 | Chin |
| 2010/0087798 A1 | 4/2010 | Adams et al. |
| 2010/0152647 A1 | 6/2010 | Shener et al. |
| 2010/0292536 A1* | 11/2010 | Yamakawa ...... A61M 25/10187 600/116 |
| 2011/0166419 A1 | 7/2011 | Reif et al. |
| 2012/0078038 A1 | 3/2012 | Sahney et al. |
| 2013/0131452 A1 | 5/2013 | Kuroda et al. |
| 2013/0267894 A1* | 10/2013 | Woolford ............... A61B 1/015 604/67 |
| 2013/0303852 A1* | 11/2013 | Hiraga ............... A61B 1/00068 600/118 |
| 2014/0031834 A1 | 1/2014 | Germain et al. |
| 2014/0303551 A1* | 10/2014 | Germain ............. A61M 3/0212 604/30 |
| 2015/0119795 A1* | 4/2015 | Germain ............. A61M 3/0212 604/28 |
| 2017/0000959 A1* | 1/2017 | Mantell ............. A61B 17/3474 |
| 2020/0237977 A1* | 7/2020 | Panotopoulos ..... A61M 1/0058 |

\* cited by examiner

SYSTEMS AND METHODS FOR MEASURING AND CONTROLLING PRESSURE WITHIN AN INTERNAL BODY CAVITY

BACKGROUND

Technical Field

The present disclosure relates generally to surgery within an internal body cavity. In particular, the present disclosure relates to systems and methods for measuring and controlling pressure within an internal body cavity.

Background of Related Art

Surgical procedures, such as tissue resection, may be performed within an internal body cavity, such as a uterus, by inserting an endoscope into the uterus and passing a tissue resection device through the endoscope and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

If the outflow of fluid from the uterus is greater than the inflow of fluid, the uterus may collapse, making visualization and tissue resection difficult. On the other hand, if the inflow of fluid is greater than the outflow of fluid, excess fluid can enter the patient's vascular system and result in serious complications or death. Thus, the inflow and outflow of fluid to/from the uterus is monitored and controlled to maintain proper distension of the uterus during the tissue resection procedure.

SUMMARY

As used herein, the term "distal" refers to the portion that is described which is further from a user, while the term "proximal" refers to the portion that is described which is closer to a user. Further, to the extent consistent, any or all of the aspects described herein may be used in conjunction with any or all of the other aspects described herein.

Provided in accordance with aspects of the present disclosure is a system including an endoscope configured for insertion into an internal body cavity and a fluid management system. The fluid management system includes a pump configured to pump fluid through the endoscope into the internal body cavity and a controller configured to determine a pressure within the internal body cavity based upon a current feedback signal received from the pump.

In an aspect of the present disclosure, the controller is further configured to compare the determined pressure to a target pressure or a target pressure range, and control the pump to maintain the determined pressure at the target pressure or within the target pressure range.

In another aspect of the present disclosure, the controller includes an input configured to receive the target pressure or the target pressure range.

In still another aspect of the present disclosure, the controller is configured to determine the pressure based upon the current feedback signal and correlating information stored in a memory of the controller.

In yet another aspect of the present disclosure, the pump includes a peristaltic pump. Additionally or alternatively, the pump includes a brushless DC motor.

In still yet another aspect of the present disclosure, the system further includes a surgical instrument configured for insertion through the endoscope. The surgical instrument may be a resector and may be configured to resect tissue and withdraw the resected tissue and fluid from the internal body cavity.

In another aspect of the present disclosure, the endoscope is further configured to withdraw fluid from the internal body cavity.

A method provided in accordance with aspects of the present disclosure includes supplying a drive signal to a pump to pump fluid into an internal body cavity, receiving a current feedback signal from the pump, and determining a pressure within the internal body cavity based on the current feedback signal.

In an aspect of the present disclosure, the method further includes comparing the determined pressure to a target pressure or a target pressure range and controlling the pump to maintain the determined pressure at the target pressure or within the target pressure range.

In another aspect of the present disclosure, the method further includes receiving the target pressure or the target pressure range from a user.

In still another aspect of the present disclosure, controlling the pump includes varying the drive signal.

In yet another aspect of the present disclosure, determining the pressure includes correlating the current feedback signal to the determined pressure using correlating information stored in a memory.

BRIEF DESCRIPTION OF THE DRAWINGS

Various aspects and features of the present disclosure are described hereinbelow with reference to the drawings wherein like numerals designate identical or corresponding elements in each of the several views and:

FIG. 3 is an enlarged, perspective view of the area of detail indicated as "3" in

FIG. 1;

DETAILED DESCRIPTION

Figure 1:
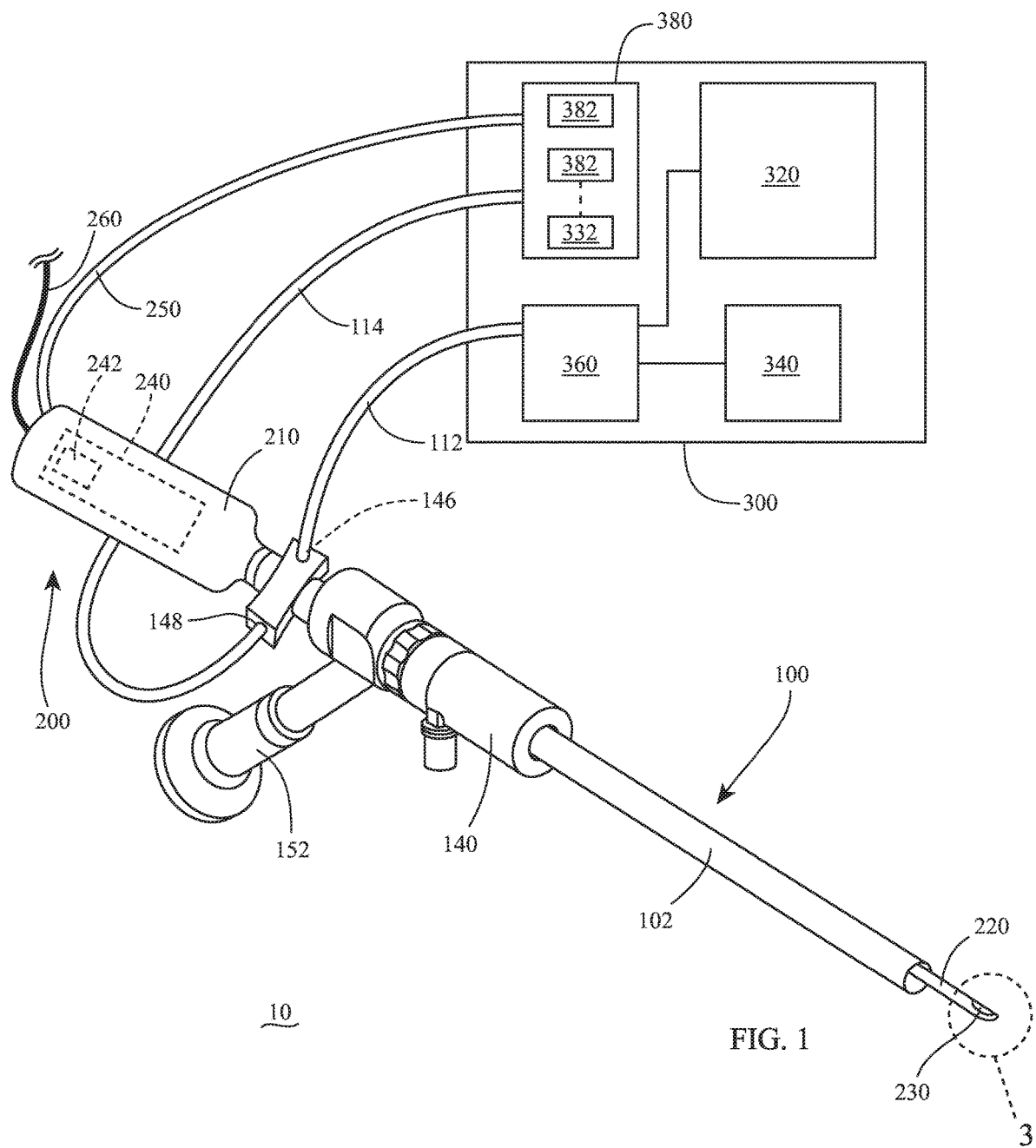
FIG. 1 is a perspective view of a surgical system provided in accordance with the present disclosure including a surgical instrument, an endoscope, and a fluid management system.

Referring to FIG. 1, a surgical system 10 provided in accordance with the present disclosure includes an endoscope 100, a surgical instrument 200 insertable through endoscope 100, and a fluid management system 300 configured to supply fluid to and receive fluid from endoscope 100 and/or surgical instrument 200. Endoscope 100 is detailed herein as a hysteroscope configured for use in gynecological surgical procedures within the uterus; surgical instrument 200 is detailed herein as a tissue resecting instrument configured for resecting tissue within the uterus; and fluid management system 300 is detailed herein as configured to control fluid flow to maintain proper distension of the uterus to facilitating tissue resection and create a visible working space. However, it is understood that the aspects and features of the present disclosure are equally applicable for use in other surgical procedures, within other internal body cavities, and/or with different instrumentation.

Endoscope 100 includes an elongated tubular member 102 and a proximal body 140. Proximal body 140 includes an inflow valve 146, an outflow valve 148, and an arm 152 that is configured to connect to an imaging device (e.g., a camera) to capture images received via a visualization device, e.g., optics 110, extending through elongated tubular member 102.

Figure 2:
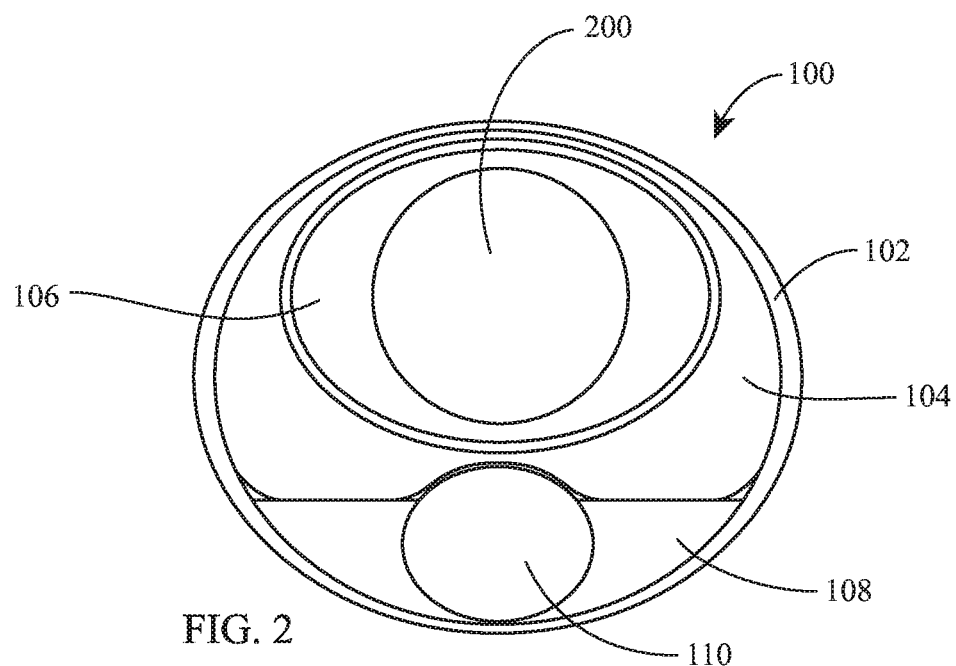
FIG. 2 is a distal end view of the endoscope including the surgical instrument disposed therein.
Figure 4:
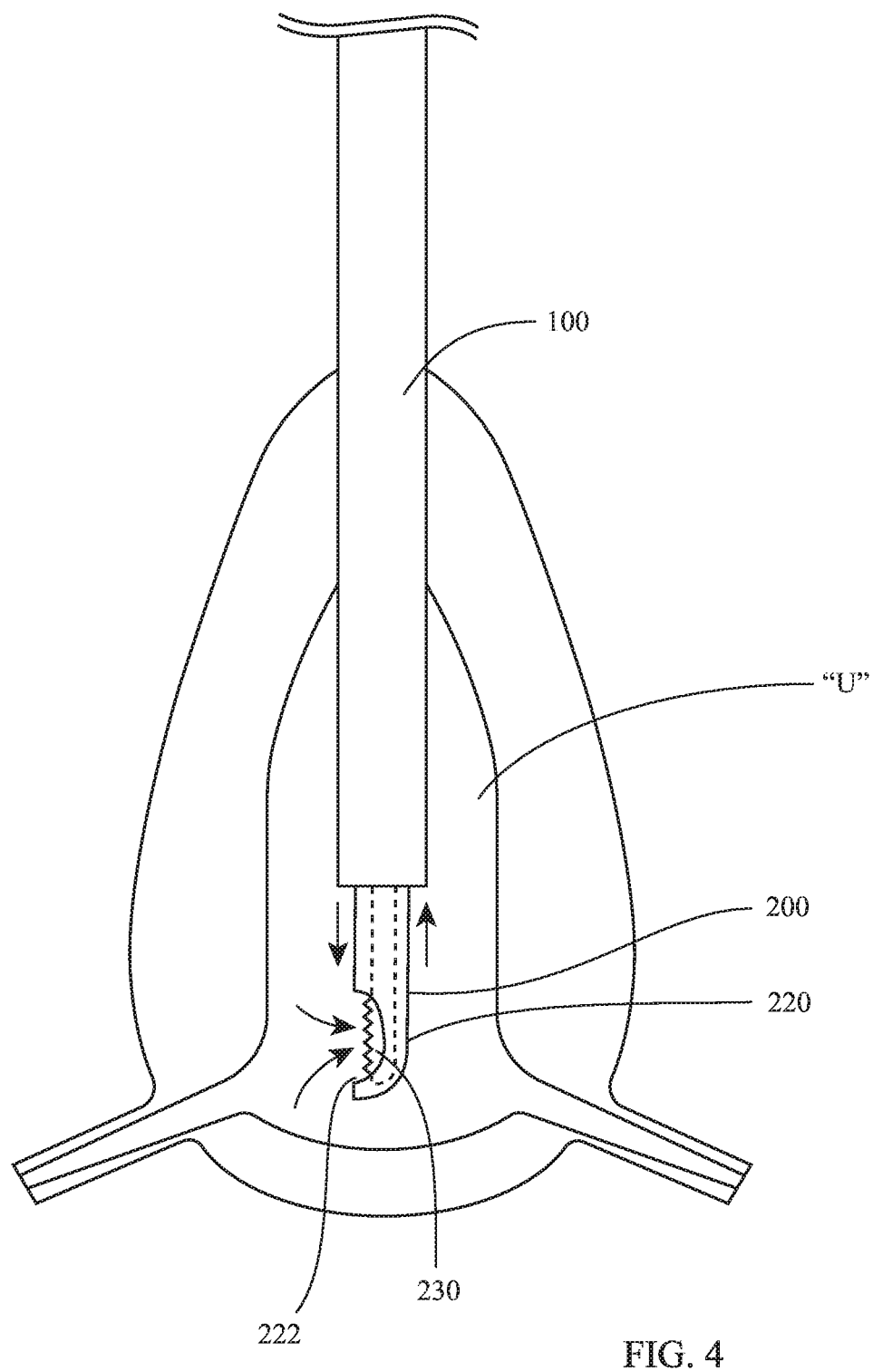
FIG. 4 is a side view of the distal end portion of the endoscope, including the surgical instrument disposed therein, shown positioned within a uterus for resecting tissue therefrom.

Referring also to FIG. 2, elongated tubular member 102 of endoscope 100 defines a first channel 104 for fluid inflow, a second channel 106 that is shared between fluid outflow and instrument access, e.g., for instrument 200, and a third channel 108 housing optics 110. First channel 104 is coupled to inflow valve 146 to enable the introduction of fluid into the uterus "U" (FIG. 4) via first channel 104. More specifically, tubing 112 is coupled between fluid management system 300 and inflow valve 146 to deliver fluid through inflow valve 146 and first channel 104 into the uterus "U" (FIG. 4). Second channel 106 is coupled to outflow valve 148 to enable the return of fluid to fluid management system 300 via second channel 106, outflow valve 148, and tubing 114 coupled between outflow valve 148 and fluid management system 300. Optics 110 extend through third channel 108 to enable visualization at the distal end of elongated tubular member 102.

Figure 3:
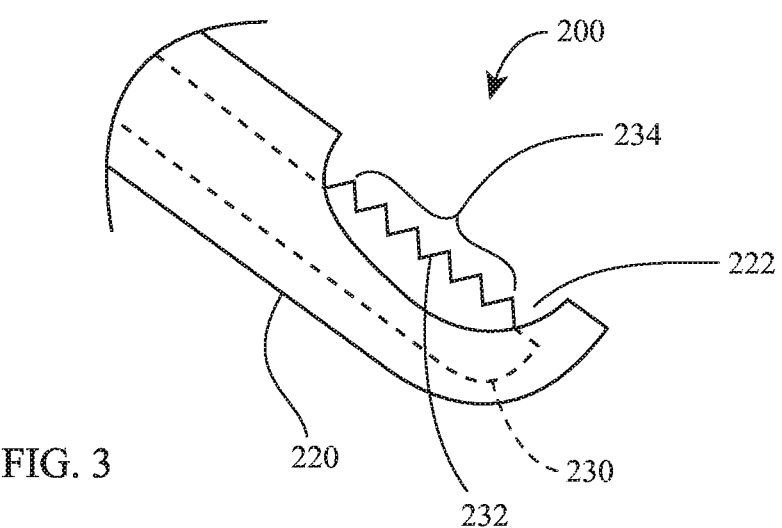

With reference to FIGS. 1 and 3, surgical instrument 200 generally includes a housing 210, a shaft 220, a cutting member 230, a drive mechanism 240, an outflow tube 250, and a cable 260. Housing 210 houses drive mechanism 240 therein and functions as a handle to enable a user to grasp surgical instrument 200. Drive mechanism 240 includes a motor 242 and is operably coupled to cutting member 230 to drive rotation and/or translation of cutting member 230 relative to shaft 220. Drive mechanism 240 is adapted to connect to a control unit (not shown) via cable 260 for powering and controlling motor 242, although surgical instrument 200 may alternatively be battery powered or manually powered. A suction source (not shown) incorporated into the control unit (not shown), or any other suitable vacuum-creating mechanism, may also be provided to facilitate withdrawal of fluid, tissue, and debris through surgical instrument 200 and outflow tube 250, as detailed below.

Shaft 220 of tissue resecting instrument 200 extends distally from housing 210 and, in embodiments, is stationary relative to housing 210, although other configurations are also contemplated. Shaft 220 defines a window 222 through a side wall thereof towards a distal end thereof to provide access to cutting member 230 which is rotatably and/or translatably disposed within shaft 220 and, as noted above, operably coupled to drive mechanism 240. Cutting member 230 defines an opening 232 providing access to the interior thereof and may include a serrated cutting edge 234 surrounding opening 232, although other suitable cutting edge configurations are also contemplated. Alternatively or additionally, shaft 220 may include a cutting edge defined about window 222. In use, upon activation, tissue is drawn through window 222 of shaft 220 and into opening 232 of cutting member 230. As tissue is drawn into opening 232 of cutting member 230, the tissue is resected via the rotation and/or translation of cutting member 230 relative to shaft 220, thus enabling the resected tissue to be drawn proximally through cutting member 230, along with fluid and debris. The resected tissue and fluid and debris are drawn proximally through cutting member 230 into outflow tube 250 and, ultimately, to one or more collection canisters 382 of fluid management system 300.

Outflow tube 250 communicates with the interior lumen of shaft 220 and/or the interior lumen of cutting member 230 to enable the withdrawal of fluid, tissue, and debris from the uterus "U" (FIG. 4), as noted above. Outflow tube 250 is operably coupled to fluid management system 300 and, more specifically, one or more collection canisters 382 thereof that are configured to collect the fluid, tissue, and debris withdrawn from the uterus "U" (FIG. 4).

Referring to FIGS. 1-4, in use, endoscope 100 is positioned within an internal body cavity, e.g., a uterus "U." Once endoscope 100 is positioned in this manner, surgical instrument 200 is inserted through first channel 104 of endoscope 100 such that the distal end of surgical instrument 200 extends distally from endoscope 100. In order to resect tissue, fluid is pumped from fluid management system 300, through tubing 112, inflow valve 146, and first channel 104, into the uterus "U" to distend the uterus "U." Surgical instrument 200 is then activated to draw tissue through window 222 of shaft 220 and into cutting member 230, resect the tissue via the rotation and/or translation of cutting member 230 relative to shaft 220, and draw the resected tissue proximally through cutting member 230, along with fluid and debris, such that the resected tissue and fluid and debris travel through outflow tube 250 and are deposited in one or more of collection chambers 382 of fluid management system 300. Outflow of fluid from the uterus "U" is provided via second channel 106 of endoscope 100. More specifically, outflow fluid flows from the uterus "U" into and through second channel 106, outflow valve 148, and tubing 114 for depositing in one or more of collection canisters 382.

Figure 5:
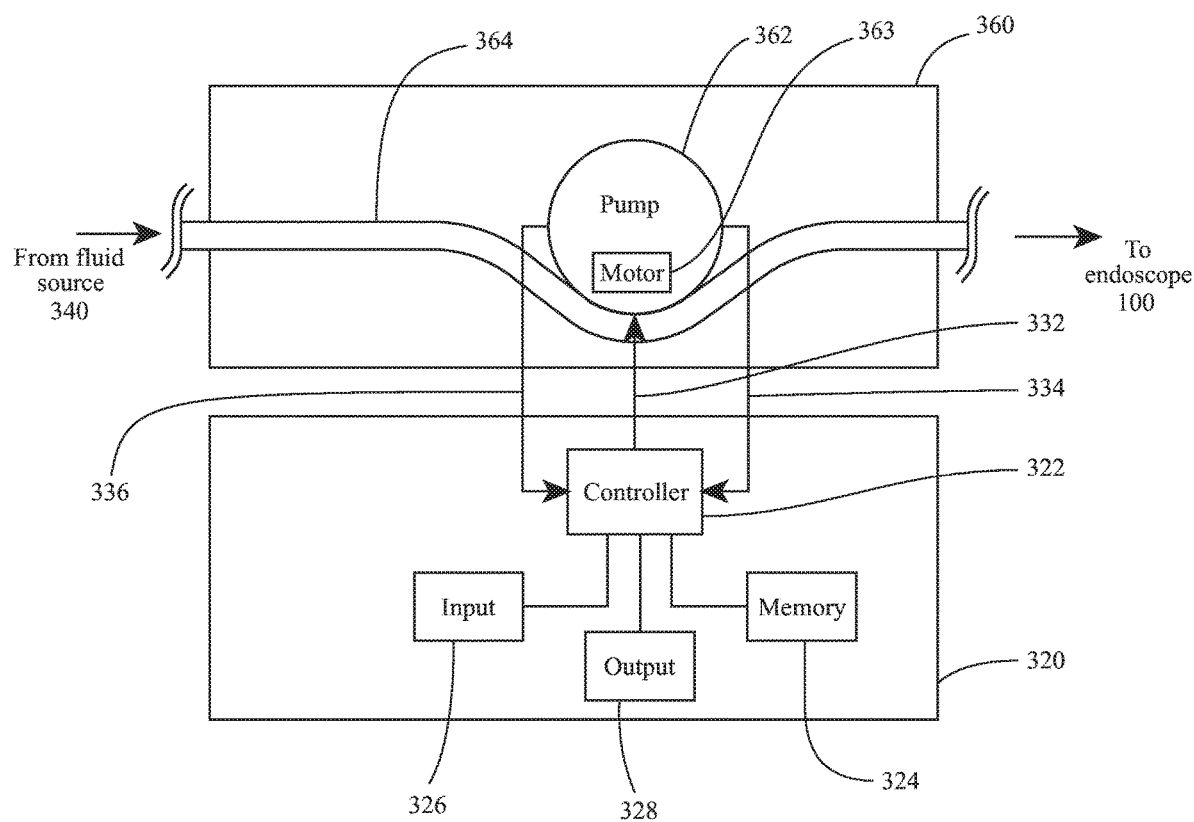
FIG. 5 is a schematic illustration of a control assembly and a pump assembly of the fluid management system.

With reference to FIGS. 1 and 5, fluid management system 300 includes a control unit 320, a fluid source 340, a pump assembly 360, and a collection assembly 380 including one or more collection canisters 382. Control unit 320, as detailed below, is configured to maintain a selected pressure within the uterus "U" (FIG. 4). Fluid source 340 includes a reservoir storing a suitable fluid such as, for example, saline, sorbitol, or glycine. Pump assembly 360 is configured to pump fluid from the fluid source 340 to inflow tubing 112 for delivery to the uterus "U" (FIG. 4) via first channel 104 of endoscope 100 (FIG. 3). Collection assembly 380, as noted above, includes one or more collection canisters 382 for collecting tissue, fluid, and debris returned from uterus "U" (FIG. 4) via outflow tube 250 of surgical instrument 200 and tubing 114 of endoscope 100.

Referring in particular to FIG. 5, control unit 320 includes a controller 322, a memory 324, an input 326, and an output 328. Controller 322 may include, for example, a microcontroller and a storage medium storing instructions to be executed by the microcontroller. Controller 322 is configured to receive input information via input 326, provide output(s) via output 328, and control a drive signal 332 provided to motor assembly 360 based on the input information, information stored in memory 324, and/or feedback signals 334, 336 received from pump assembly 360.

Input 326 may include a touch-screen display, keypad, wired or wireless port for communicating with an external device, and/or other suitable input capable of receiving input information such as, for example, an intra-uterine pressure value or an intra-uterine pressure range to be maintained. Output 328 may include a display screen, one or more LED's, an audio speaker, and/or any other suitable output for communicating body cavity pressure information, alerts, etc. to a user.

Pump assembly 360, as noted above, is configured to pump fluid from the fluid source 340 to inflow tubing 112 for delivery to the uterus "U" (FIG. 4) via first channel 104 of endoscope 100 (FIG. 3). Pump assembly 360 includes a pump 362 and tubing 364 and is coupled between fluid source 340 and endoscope 100 to enable fluid to be pumped from fluid source 340 to endoscope 100 for delivery into the uterus "U" (FIG. 4.) Pump 362 may be configured as a peristaltic pump driven by a brushless DC motor 363, although other suitable pump configurations are also contemplated. Motor 363 of pump 362 receives the drive signal 332 from controller 322 to drive pump 362.

Controller 322 is configured to receive a first feedback signal 334 from motor 363 indicative of a current applied to motor 363, and one or more second or hall feedback signals 336 indicative of a position of motor 363. Second feedback signal(s) 336 enable controller 322 to adjust the drive signal 332 to control motor 363 and, thus, pump 362. First feedback signal 334, which indicates a current applied to motor 363, is utilized to determine the pressure within the uterus "U" (intra-uterine pressure). More specifically, the current provided to motor 363 to drive pump 362 is proportional to the torque motor 363 delivers which, in turn, is proportional to the pressure of fluid pumped through tubing 364 to endoscope 100. Using these proportional values (correlating information), the pressure of fluid pumped through tubing 364 can be determined from the current applied to motor 363 and, accounting for the impedance through endoscope 100, the intra-uterine pressure can be determined therefrom.

Memory 324 is configured to store calibration information regarding pump 362 and impedance information regarding endoscope 100 (and, in embodiments, tubing 112, 364) to enable controller 322 to determine the intra-uterine pressure based on the current feedback signal 334 received from pump assembly 360, without the need for pressure sensors. Thus, controller 322 can adjust the drive signal 332 provided to motor assembly 360, if necessary, to maintain a selected intra-uterine pressure or to maintain the intra-uterine pressure within a selected range. In embodiments, the selected intra-uterine pressure is from about 90 mmHg to about 150 mmHg. In embodiments, the intra-uterine pressure range is from about 90 mmHg to about 150 mmHg, or a suitable sub-range within the about 90 mmHg to about 150 mmHg range.

Figure 6:
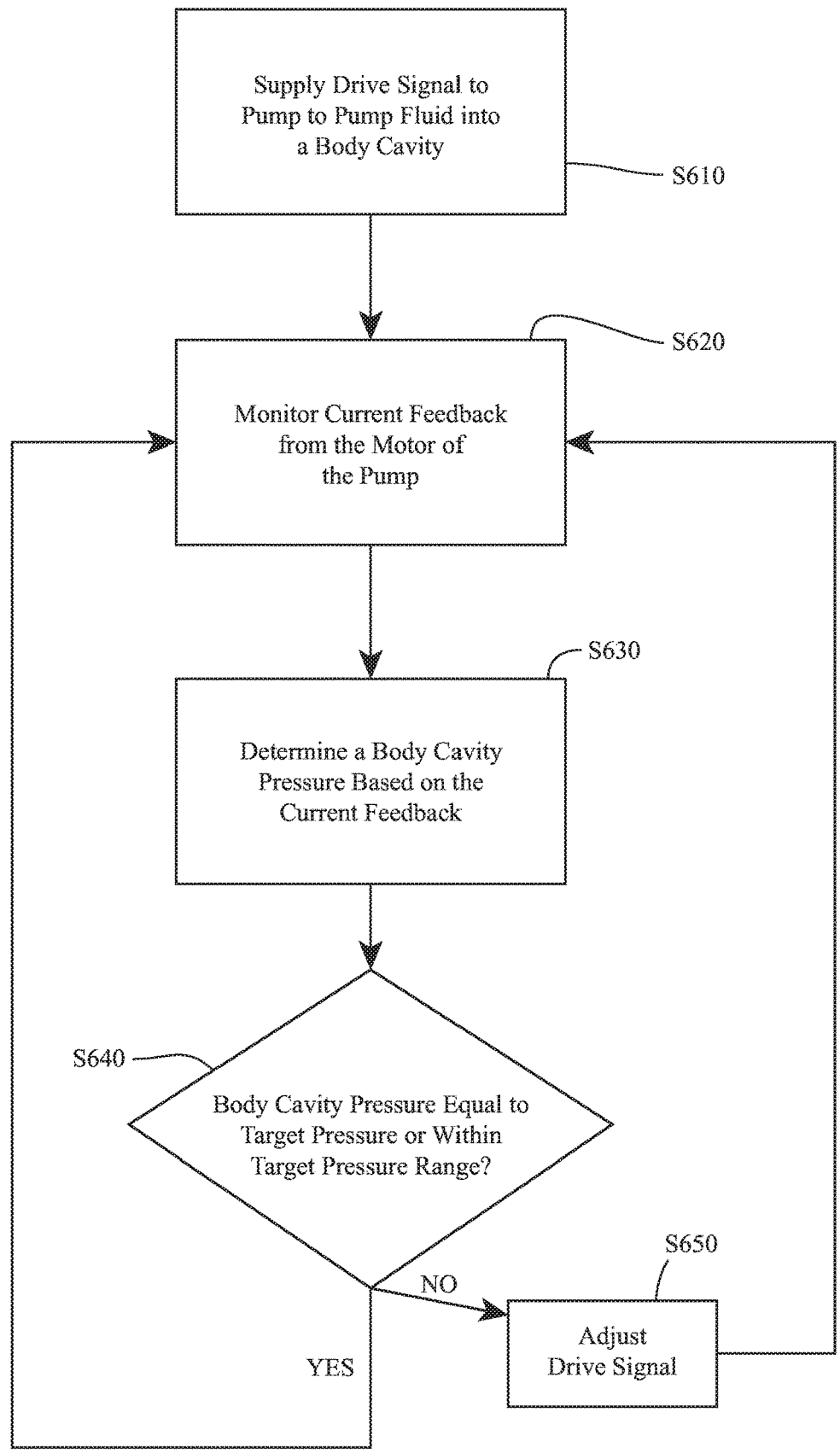
FIG. 6 is a flow diagram illustrating a method in accordance with the present disclosure.

Turning to FIG. 6, in conjunction with FIGS. 1, 4, and 5, in use, an intra-uterine pressure or intra-uterine pressure range is input to fluid management system 300 via input 326 of control unit 320 or is retrieved from memory 324 of control unit 320. Next, with endoscope 100 positioned within an internal body cavity, e.g., uterus "U," and surgical instrument 200 inserted therethrough, drive signal 332 is provided from controller 322 to motor 363 of pump 362 to pump fluid from fluid source 340, through tubing 112, inflow valve 146, and first channel 104 (FIG. 2), into the body cavity, e.g., uterus "U," as indicated at S610. With fluid flowing into the uterus "U," surgical instrument 200 may be activated to resect tissue and remove the resected tissue along with fluid and debris from the uterus "U," while fluid is withdrawn out of the uterus "U" through second channel 106 (FIG. 2) of endoscope 100 for collection in one or more of collection canisters 382.

As pump 362 is driven to pump fluid into the body cavity, controller 322 monitors the current feedback signal 334 from motor 363 of pump 362, as indicated at S620. The current feedback signal 334, together with information retrieved from memory 324, enables controller 322 to determine the pressure within the body cavity, e.g., the intra-uterine pressure, as indicated at S630. Controller 322 may determine the intra-uterine pressure continuously or periodically at a suitable interval.

As indicated at S640, the pressure determined in S630 is compared to the target pressure or target pressure range to determine whether the determined pressure is equal to the target pressure or within the target pressure range. If "YES," no modification of the drive signal 332 is required (other than the ongoing control provided by controller 322 via second feedback signals 336), and the process returns to S620 to continuously or intermittently monitor and control the pressure within the body cavity. If "NO," as indicated in S650, the drive signal 332 is adjusted to increase or decrease the output of pump 362, as necessary, to increase or decrease the pressure within the body cavity until the pressure is equal to the target pressure or within the target pressure range. Once this is achieved, the process again returns to S620 to continuously or intermittently monitor and control the pressure within the body cavity.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A system, comprising:
   an endoscope configured for insertion into a uterus; and
   a fluid management system, including:
      a fluid source; and
      a pump assembly connected with the fluid source, the pump assembly including:
         a pump configured to pump fluid from the fluid source to the endoscope;
         a tube coupled between the fluid source and the endoscope to enable fluid to be pumped from the fluid source to the endoscope for delivery of the fluid into the uterus;
         a motor configured to drive the pump; and
         a controller configured to provide a drive signal to the motor to drive the pump for pumping the fluid through the tube and into the uterus via the endoscope, wherein the controller is configured to receive:
            a first feedback signal generated by the motor in response to the drive signal provided to the motor, the first feedback signal indicative of a current applied to the motor that is proportional to a torque generated by the motor in response to the current applied to the motor, wherein the torque generated by the motor is, in turn, proportional to a pressure of the fluid pumped through the tube and into the uterus via the endoscope; and
            one or more second feedback signals generated by the motor in response to the drive signal provided to the motor, the one or more second feedback signals indicative of a position of the motor, wherein the controller is configured, in response to the one or more second feedback signals, to adjust the drive signal provided to the motor to control pumping of the fluid through the tube and into the uterus via the endoscope, thereby regulating a pressure of the fluid within the uterus.

2. The system of claim 1, wherein the pump includes a peristaltic pump.

3. The system of claim 1, wherein the pump includes a brushless DC motor.

4. The system of claim 1, further including a surgical instrument configured for insertion through the endoscope.

5. The system of claim 4, wherein the surgical instrument is a tissue resector.

6. The system of claim 5, wherein the tissue resector is configured to resect tissue and withdraw the resected tissue and the fluid from the uterus.

7. The system of claim 1, wherein the endoscope is further configured to withdraw the fluid from the uterus.

8. A fluid management system, comprising:
a fluid source; and
a pump assembly connected with the fluid source, the pump assembly including:
  a pump configured to pump fluid from the fluid source to an endoscope;
  a tube extending from the fluid source and configured to be connected with the endoscope to enable fluid to be pumped from the fluid source to the endoscope for delivery of the fluid into a uterus;
  a motor configured to drive the pump; and
  a controller configured to provide a drive signal to the motor to drive the pump for pumping the fluid through the tube and into the uterus via the endoscope, wherein the controller is configured to receive:
    a first feedback signal generated by the motor in response to the drive signal provided to the motor, the first feedback signal indicative of a current applied to the motor that is proportional to a torque generated by the motor in response to the current applied to the motor, wherein the torque generated by the motor is, in turn, proportional to a pressure of the fluid pumped through the tube and into the uterus via the endoscope; and
    one or more second feedback signals generated by the motor in response to the drive signal provided to the motor, the one or more second feedback signals indicative of a position of the motor, wherein the controller is configured, in response to the one or more second feedback signals, to adjust the drive signal provided to the motor to control pumping of the fluid through the tube and into the uterus via the endoscope, thereby regulating a pressure of the fluid within the uterus.

9. The fluid management system of claim 8, wherein the pump includes a peristaltic pump.

10. The fluid management system of claim 8, wherein the pump includes a brushless DC motor.

11. The fluid management system of claim 8, further including a memory storing calibration information for the pump.

12. The fluid management system of claim 11, wherein the memory is configured to store impedance information for the endoscope.

* * * * *